United States Patent [19]
Latham, Jr.

[11]  4,285,464
[45]  Aug. 25, 1981

[54] APPARATUS FOR SEPARATION OF BLOOD INTO COMPONENTS THEREOF

[75] Inventor: Allen Latham, Jr., Jamaica Plain, Mass.

[73] Assignee: Haemonetics Corporation, Braintree, Mass.

[21] Appl. No.: 155,069

[22] Filed: Jun. 2, 1980

Related U.S. Application Data

[62] Division of Ser. No. 5,126, Jan. 22, 1979, abandoned.

[51] Int. Cl.³ .......................... B04B 9/12; B04B 11/02
[52] U.S. Cl. ................................. 233/26; 128/214 R; 128/272
[58] Field of Search ....................... 233/23 A, 26, 23 R, 233/24, 16, 17, 19 R; 128/214 F, 214 D, 272, 214 R

[56] References Cited

U.S. PATENT DOCUMENTS

| | | | |
|---|---|---|---|
| 3,190,546 | 6/1965 | Raccuglia | 233/26 |
| 3,211,368 | 10/1965 | Shanley | 233/26 |
| 4,146,172 | 3/1979 | Cullis | 128/214 |

Primary Examiner—Robert W. Jenkins
Attorney, Agent, or Firm—Hamilton, Brook, Smith & Reynolds

[57] ABSTRACT

Apparatus is disclosed for centrifugally separating blood into a first blood component, such as a plasma-rich component, and a second blood component, such as a plasma-poor component. This apparatus employs a self-balancing centrifuge intended to be used immediately adjacent to a blood donor. The blood pathway is completely disposable and includes a phlebotomy needle and blood compatible tubing connecting the phlebotomy needle to a flexible blood processing bag designed to be supported within a contoured processing chamber in the centrifuge rotor so that second blood component travels along a short internal bag dimension to achieve separation. A displacement chamber having a fluid operated diaphram is also positioned within the blood processing chamber of the centrifuge rotor. Separated first blood component can be expressed from the flexible blood bag by movement of the diaphram and collected in a receiver container as the centrifuge rotor spins. The centrifuge rotor can then be stopped to allow return of second blood component to the donor.

5 Claims, 10 Drawing Figures

APPARATUS FOR SEPARATION OF BLOOD INTO COMPONENTS THEREOF

This is a division of application Ser. No. 005,126, filed Jan. 22, 1979.

BACKGROUND OF THE INVENTION

1. Field of the Invention

This invention is in the field of blood processing and more particularly relates to the separation of blood, including whole blood, into two or more components.

2. Description of the Prior Art

Whole human blood includes at least three types of specialized cells. These are the red blood cells, white blood cells and platelets. All of these cells are suspended in plasma, a complex aqueous solution of proteins and other molecular substances.

Until relatively recently, blood transfusions have been given using whole blood. There is, however, growing acceptance within the medical profession for transfusing only those blood components required by a particular patient instead of transfusing whole blood. Transfusing only those blood components necessary preserves the available supply of blood, and in many cases, it is better for the patient. Before blood component transfusions can be widely employed, however, satisfactory blood separation techniques and apparatus must evolve.

One desirable blood separation in plasmapheresis which is the separation of whole blood into a plasma-rich component and a plasma-poor component. Typically, the plasma-rich component is retained for later use and the plasma-poor component is returned to the donor.

Presently, plasmapheresis is performed on a large scale using satellite pouch systems. A variety of satellite pouch plasmapheresis systems have been patented, and some typical examples are those systems described in U.S. Pat. No. 3,190,546 to Raccuglia et al.; U.S. Pat. No. 3,211,368 to Shanley; and U.S. Pat. No. 3,545,671 to Ross. With such systems, whole blood is withdrawn from a donor and flows to a pouch containing an anti-coagulant. The pouch is then disconnected from the donor phlebotomy line, centrifuged in a swinging bucket type of centrifuge in which cells must travel about half the long dimension of the pouch, typically about 12 cm. The centrifuge must then be gently slowed to a stop and the pouch carefully lifted from the bucket of the centrifuge while avoiding remixing of the two components. The pouch is mounted in a plasma expressor and a supernatant plasma fraction is expressed into a connected plasma pouch, care being given to clamp off the connecting tube between the pouches just before plasma-poor component passes over. The pouch containing the plasma-poor component is then reconnected to the phlebotomy line so that the plasma-poor component can be returned to the donor.

It has become customary with satellite pouch systems to carry out this sequence of steps twice for each donor. Typically, one unit, or about 500 ml of whole blood is withdrawn, anti-coagulated and separated. Approximately 250 ml of plasma-rich component is obtained and the plasma-poor component is returned to the donor. Subsequently, another unit of whole blood is withdrawn and processed in a similar manner. Using such techniques with satellite pouch systems, it often takes approximately 1½ hours to obtain 500 ml of separated plasma-rich component and to return the plasma-poor component to the door, even though the time for donating a unit of whole blood is only about 20 minutes. This relatively long processing time imposes a major limitation on volunteer donor recruitment. Additionally, because the blood pouch is disconnected from the donor at the end of each withdraw cycle and transported to and from a separate centrifuge room for centrifugation, there is always the danger of returning blood components to a donor which are not his own. Satellite pouch systems require particularly careful handling of the pouch containing separated plasma-rich and plasma-poor components to avoid remixing thereby ruining the separation.

Blood cell separation systems, both continuous and intermittent flow, have been placed in widespread use but have not been accepted for widespread application in plasmapheresis because the disposable blood pathways used are too expensive relative to the satellite pouch systems. An example of a recently developed plasmapheresis apparatus is described by Latham in U.S. Pat. No. 4,086,924. In this apparatus, whole blood can be withdrawn from a donor using a phlebotomy needle and pressure cuff. The whole blood is anticoagulated and transported by a blood pump to a plasmapheresis centrifuge where it is separated into plasma-rich and plasma-poor components. Separated plasma-rich component is stored in a plasma container. When a predetermined quantity of separated plasma-rich component has been obtained, cycle control means immediately switch from the withdraw cycle to a return cycle. The cycle control means also immediately switch from the return cycle to either a withdraw cycle or a standby cycle in response to a signal from monitoring means indicating that the return of plasma-poor component has been completed. The manufacturing costs of the disposable blood pathway for this system has been greater than that for a satellite pouch system, however, and although the Latham system is attractive because of the short (30 min.) donor time required, it has involved too much expense to be accepted for use on a wide scale.

One main reason for the relatively high expense of the disposable blood pathway in prior blood separation systems of the Latham type relates to the requirement for a specially manufactured blood centrifuge bowl. Many times, for example, parts for these are injection molded from relatively expensive materials, such as polycarbonate, which adds a major element of expense to the disposable blood pathway. Another reason for the relatively high expense in the Latham system is the requirement for precisely manufactured rotary seals to pass blood in and plasma-rich component out of the centrifuge bowl as it is spinning. It is theoretically possible to eliminate such inordinate expense, therefore, by employing a relatively inexpensive, disposable blood bag as the processing chamber and by eliminating the requirement for a rotary seal. Blood separation systems have been designed with one or both of these in mind, but such systems have invariably suffered from their own set of problems and disadvantages.

Mitchell et al., in U.S. Pat. No. 3,674,197, for example, point out some problems encountered with attempts to use standard flexible blood bags in a centrifuge rotor. The problems mentioned relate to the necessity to properly support the liquid filled bags because they are subjected to various pressures and forces during centrifugation which are not evenly distributed.

The shifting of position of the flexible blood bags causes wrinkles and folds in the bag material with consequent imbalancing of the rotor. The mitchell et al. invention disclosed in this patent relates to contoured shoes which surround a cylindrical flexible blood processing bag to alleviate such problems. However, there is no attempt by these patentees to provide a contoured blood processing chamber which supports a standard blood bag in a position to achieve centrifugal separation by minimizing the distance that the blood components are required to travel during centrifugation.

Another approach to using a flexible blood processing bag in a centrifugation system is disclosed by Jones et al. in U.S. Pat. No. 3,737,096. The highly specialized system disclosed therein is a cell washing system in which a flexible blood bag receives fluid and has fluid withdrawn from it during operation of the centrifuge. The volume of the processing chamber in this centrifuge is adjusted by a flexible membrane connected to a displacement fluid which expands or contracts, respectively, in response to introduction of or withdrawal of a displacement fluid. This system has the disadvantage of requiring a rotary seal. Additionally, the flexible bag is relatively complex and does not have a design intended to minimize the distance which blood components travel during separation.

As can be appreciated from the above discussion, there has been very considerable effort applied to developing new blood processing systems. Despite this, none of the systems developed heretofore provide the combination of inexpensive disposable blood processing sets, rapid separation, ease of making a fine cut between different blood components and the capability to carry out the entire blood processing immediately adjacent to a blood donor.

SUMMARY OF THE INVENTION

The invention comprises an apparatus for separating blood, including whole blood, into a first blood component and a second blood component.

A self-balancing centrifuge having a rotor capable of spinning at speeds sufficient to effect the desired separation in a relatively short period of time without significant concomitant vibration is employed. A self-balancing centrifuge is employed because unbalanced masses of blood components and displacer fluid are introduced or withdrawn during processing which would render a conventional centrifuge useless for separation. Such a self-balancing centrifuge allows operation over wide ranges of rotating speeds and levels of unbalance so that it can be applied to various clinical procedures where the rotating speeds and their corresponding separation forces are variable.

A flexible, disposable blood processing bag is mounted in a contoured processing chamber within the centrifuge rotor. The contoured chamber is designed to support the blood bag in a position whereby second blood component traverses a short distance in the process of separation. A flexible diaphram is also positioned in the blood processing chamber of the rotor in a complementary relationship to the flexible disposable blood bag. The flexible diaphram can be moved to apply pressure to the disposable blood bag in response to the introduction of expulsion, respectively, of a displacement fluid while the centrifuge rotor is either rotating or stationary. Additionally, displacer fluid can be expelled by pumping blood into the flexible, disposable blood processing bag.

During separation, displacement fluid is introduced into the displacement chamber to drive the diaphram so that separated first component is expelled into a receiver container. Preferably, this receiver container is also positioned within the centrifuge rotor.

After separation of a desired amount of first blood component, the rotor is stopped and any changes in the blood pathway required for return of second blood component are made. Second blood component can then be returned by introducing more displacment fluid into the displacement chamber. After second component has been returned, additional blood to be separated can be introduced into the flexible blood processing bag thereby forcing displacement fluid from the displacement chamber. The separation procedures can then be repeated.

The apparatus described herein employs a completely disposable, relatively inexpensive blood pathway set, including the blood processing bag. The apparatus is extremely versatile and can be used in a great many applications where it is desirable to separate one or more components from blood, including separations requiring precise cuts between centrifugally separated fractions. Additionally, these separations can be done quickly with the apparatus stationed next to a blood donor since it can be made quite small and light in weight. This apparatus also provides the capability of separating blood cells without subjecting them to the trauma associated with intense mechanical shear experience in conventional rotary seal machines and in the more recently developed machines which eliminate the need for a rotary seal by employing a rapidly flexing umbilical cable to pass fluids to and from a centrifuge rotor. The case with which the operating technician can observe progress of the separation process and the accuracy of controlling making product cuts is also an advantage. Additionally, there is less platelet activation, less particulate contamination possible, and less anticoagulant required with this apparatus.

DESCRIPTION OF PREFERRED EMBODIMENTS

As used herein, the following terms are defined to mean:

"Self-balancing" centrifuge—a centrifuge which is designed so that once the rotor has surpassed a minimum in rotational velocity, the rotor will spin around its angular momentum vector rather than its geometrical axis of symmetry. Thus, disruptive vibrations from an unbalanced rotor, which would create intolerable vibrations in a conventional centrifuge, are not generated.

"First blood component"—one fraction of blood which it is desired to separate from another fraction;

"Second blood component"—another fraction separated from blood which is the balance after first blood component has been separated therefrom;

"Plasma-rich component"—a fraction of blood which is richer in plasma than whole blood;

"Plasma-poor component"—a fraction of blood which is poorer in plasma than whole blood.

The preferred embodiments of this invention can now be further described with specific reference to the Figures.

Figure 1:
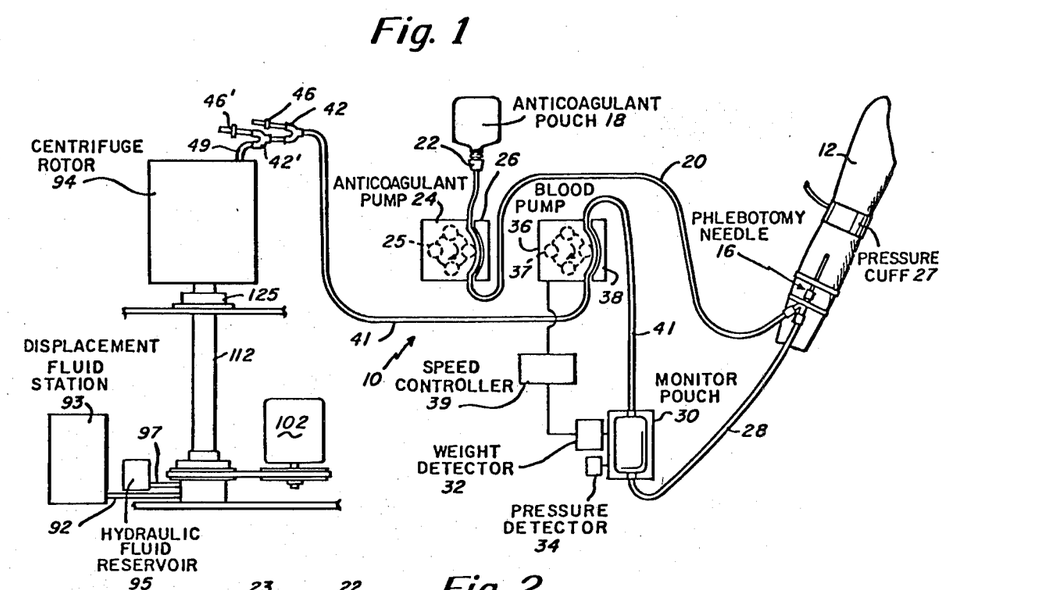
FIG. 1 is a diagrammatic illustration of an apparatus according to this invention which is suitable for plasmapheresis.

A plasmapheresis separation can be illustrated with reference to FIG. 1, which is a diagramatic illustration of plasmapheresis apparatus 10, and FIGS. 2-9, which illustrate components of the plasmapheresis apparatus 10 in more detail.

To withdraw whole blood from donor's arm 12, a standard phelbotomy needle 16 can be used with this apparatus. Phlebotomy needle 16 might be, for example, a 15-gauge, thin wall phlebotomy needle of the type which has a supply of anti-coagulant connected to it so that freshly withdrawn blood is anti-coagulated as soon as it leaves the needle. A particularly suitable phlebotomy needle of this type is described in detail in U.S. Pat. No. 3,916,892 issued to Latham.

Anti-coagulant is supplied from anti-coagulant pouch 18 to phlebotomy needle 16 through anti-coagulant tubing 20 which is connected through transparent drip chamber 22 and spike 23 to pouch 18. Transparent drip chamber 22 allows the operator to observe anti-coagulant flow. Pump 24 provides anti-coagulant pumping, when necessary, and is a roller-type pump having a movable platen 26 which is employed to clamp blood tubing 20 against rollers 25. Roller pumps of this type are described in detail in U.S. Pat. No. 3,565,286, also issued to Latham.

Prior to making the venipuncture, the disposable set of software is mounted in the permanent components of apparatus 10. Anticoagulant pouch 18 is connected by insertion of spike 23 in the conventional manner while pump platen 26 is clamped against tubing 20. Drip chamber 22 is squeezed slightly to expel some of its contained air into anticoagulant pouch 18 and then released so that a small pool of anticoagulant accumulates in the lower portion of drip chamber 22.

Blood processing bag 50 is completely collapsed by passing as much displacer fluid into pouch 69 as possible. Clamp 142 (FIG. 8) is then closed to isolate blood processing bag 50 from component receiver container 61.

Anticoagulant tubing 20 and blood tubing 28 are primed with anticoagulant by releasing pump platen 26 to allow gravity flow of anticoagulant through these lines until a small quantity collects in monitor pouch 30. Pump platen 26 is then reclamped. Throughout this priming procedure the small pool of anticoagulant in the lower section of drip chamber 22 serves to prevent entrainment of air bubbles in the stream of anticoagulant entering tubing 20 thereby assuring an air-free primed condition. Also, the operator is able to visualize the rate of anticoagulant flow through the air space in the upper portion of drip chamber 22 and thereby verify that approximately the correct anticoagulant flow is occurring at all times.

The site where the venipuncture is to be made is then prepared. After preparation, pressure cuff 27 is fastened around donor's arm 12 at a location above where phlebotomy needle 16 is to be inserted. Pressurizing gas is supplied to pressure cuff 27 from a gas canister (not shown), and the precise pressure applied is usually regulated by a pressure regulator. A gas valve may also be provided which has an open and a relief position, the latter being provided to release pressure in pressure cuff 27. A typical pressure is about 50 mm Hg which raises the pressure in the donor's veins sufficiently to facilitate the venipuncture and to boost blood flow from the donor's veins.

Plasmapheresis apparatus 10 is now started by energizing electrical systems to control pump motors, activate detectors, control pressure cuff 27, etc. Control logic may be used to monitor and control the overall operation of the plasmapheresis apparatus, if desired.

The venipuncture is them made by inserting phlebotomy needle 16 into a vein in donor's arm 12 at the previously prepared site. Freshly withdrawn, anti-coagulated, whole blood flows under venipressure from the donor through blood-compatible tubing 28 into monitor pouch 30. Monitor pouch 30 can have either a weight detector 32 or a pressure detector 34 associated with it, or both. Weight detection can be used to sense the weight of blood which is present in the monitor pouch at any given time. This in turn can be used to both activate and control the speed of blood pump 36, which is also a roller-type pump having rollers 37 and a movable platen 38. The function of pressure detector 34 will be described in conjunction with the return cycle.

At the start of a withdraw cycle, monitor pouch 30 is empty insofar as blood and blood components are concerned. As blood enters monitor pouch 30, its weight eventually reaches a threshold value which is sensed by weight detector 32. At this threshold weight, an appropriate signal is transmitted to actuate rollers 37 in blood pump 38 and to actuate rollers 25 in anti-coagulant pump 24. Blood pump 38 preferably has at least two speeds, and these speeds are determined by speed controller 39 acting in response to the signals received from weight detector 32. If the blood flow from phlebotomy needle 16 is greater than that to blood pump 36, monitor pouch 30 fills thereby becoming heavier and causing weight detector 32 to transmit signals to speed controller 39 to advance blood pump 36 to a higher speed position. If, on the other hand, pump flow from phlebotomy needle 16 is less than that to blood pump 36, monitor pouch 30 begins to empty thereby losing weight and causing signals to be transmitted to speed controller 39 to return pump 36 to a lower speed position. If monitor pouch 30 continues to lose weight even at the lower pump speed, a signal can likewise be transmitted to cause blood pump 36 to operate at a still lower speed, if available, or to be shut off entirely until monitor pouch 30 fills once again. In this way, blood is pumped from monitor pouch 30 but never from the donor. This pattern of action continues through a withdraw cycle.

Figure 2:
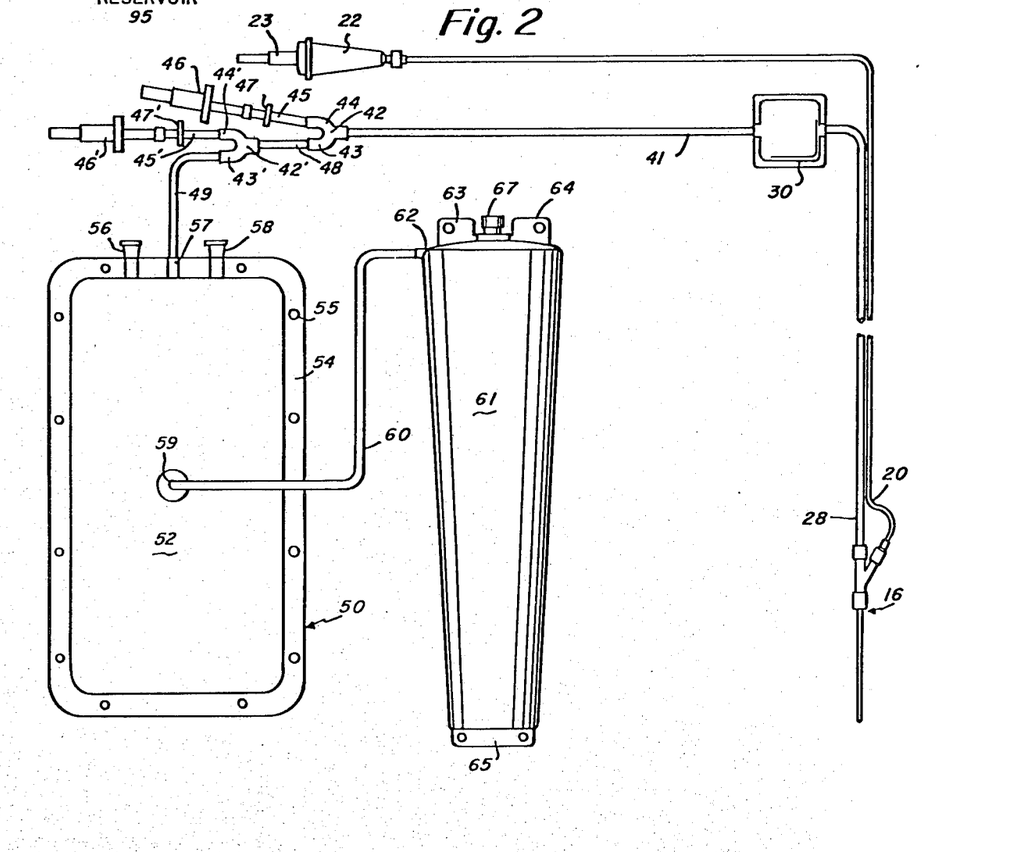
FIG. 2 is a diagrammatic view of the disposable blood pathway suitable for use in the apparatus of FIG. 1.

Anti-coagulated whole blood is pumped from monitor pouch 30 through blood compatible tubing 41 to a first U-shaped flow divider 42 having legs 43 and 44 (FIG. 2). Leg 44 is connected by tubing 45 to a spike port 46, but flow is prevented along this path at this time by clamp 47 which is closed. Whole blood does flow through leg 43 and blood-compatible tubing 48 to second U-shaped flow divider 42' having legs 43' and 44'. Leg 44' is connected by blood compatible tubing 45' to a spike port 46'. Tubing 45' is clamped off at this point in the procedure by clamp 47' so that anti-coagulated whole blood flows along leg 43' and tubing 49 to blood processing bag 50.

Figure 3:
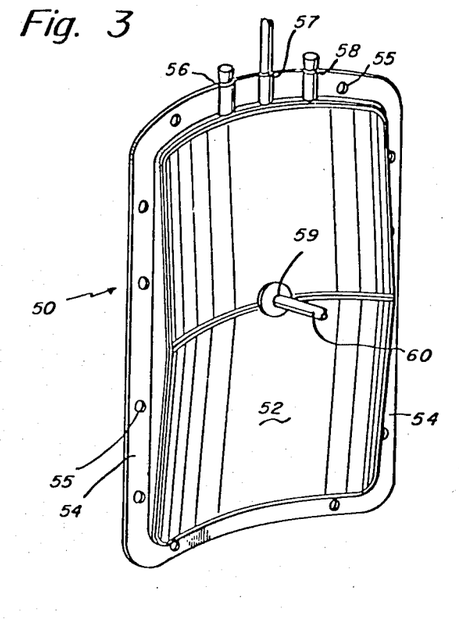
FIG. 3 is a perspective view of a flexible, disposable, blood processing bag suitable for use in the apparatus of FIG. 1.

Blood processing bag 50 can be seen in more detail in FIG. 3. Therein, it can be seen that flexible, disposable blood processing bag 50 has a front, planar, generally-rectangular panel 52. There is also a matching planar, generally-rectangular back panel, which cannot be seen, and the front and back panels are sealed together around the periphery 54 of bag 50 with a fluid-tight seal. A pattern of holes 55 is provided in sealed periphery 54 to help in registering blood processing bag 50 in its proper location within contoured shoes which are described below.

Blood processing bag 50 has three fluid ports, 56, 57 and 58, located at its top, and a fluid port 59 located approximately in the center of front panel 52. Blood-compatible tubing 60 extends from port 59 and is connected to receiver container 61 at entry port 62. The receiver container 61 can be a blow-molded container formed as a volume of revolution with its upper end larger than its lower end. Inlet port 62 is located at a point of substantially maximum diameter of receiver container 61 so that material can be withdrawn from container 61 back into blood processing pouch 50, if desired. Receiver container 61 is also provided with top flaps 63 and 64 and bottom flap 65, each having holes therein, so that container 61 can be conveniently hung from its top or bottom. Of course, these flaps are optional and may be omitted or replaced with spike ports, etc. Receiver container 61 additionally has a sterile air filter 67 which allows any air contained within the system to pass therethrough. Other receiver container geometries can be employed, of course, with any geometry designed to minimize rotor imbalance as first blood component is introduced being preferred.

Figure 4:
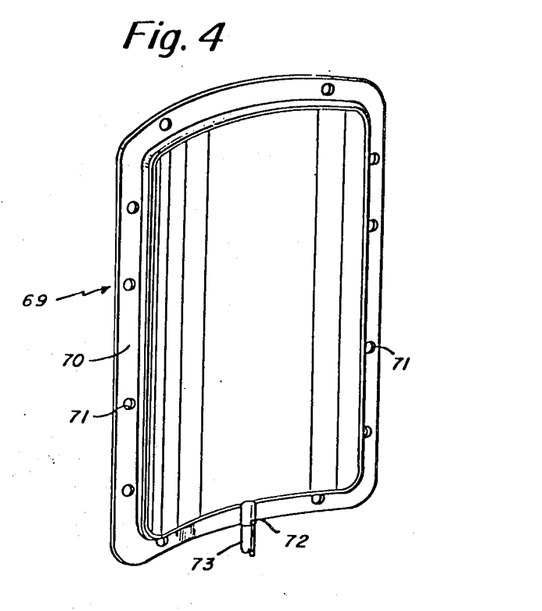
FIG. 4 is a perspective view of a flexible fluid bag suitable for use as a displacement pouch in the apparatus of FIG. 1.

FIG. 4 illustrates a flexible displacement pouch 69 which serves as a displacement chamber in plasmapheresis apparatus 10. Flexible, displacement pouch 69 is a flexible liquid bag formed from planar front and back panels and having a peripheral seal 70. Registration holes 71 are provided in the peripheral seal 70 and a single inlet/outlet port 72 is provided at the bottom to allow displacer fluid to be transported into or out of pouch 69 via displacer fluid tubing 73.

Figure 5:
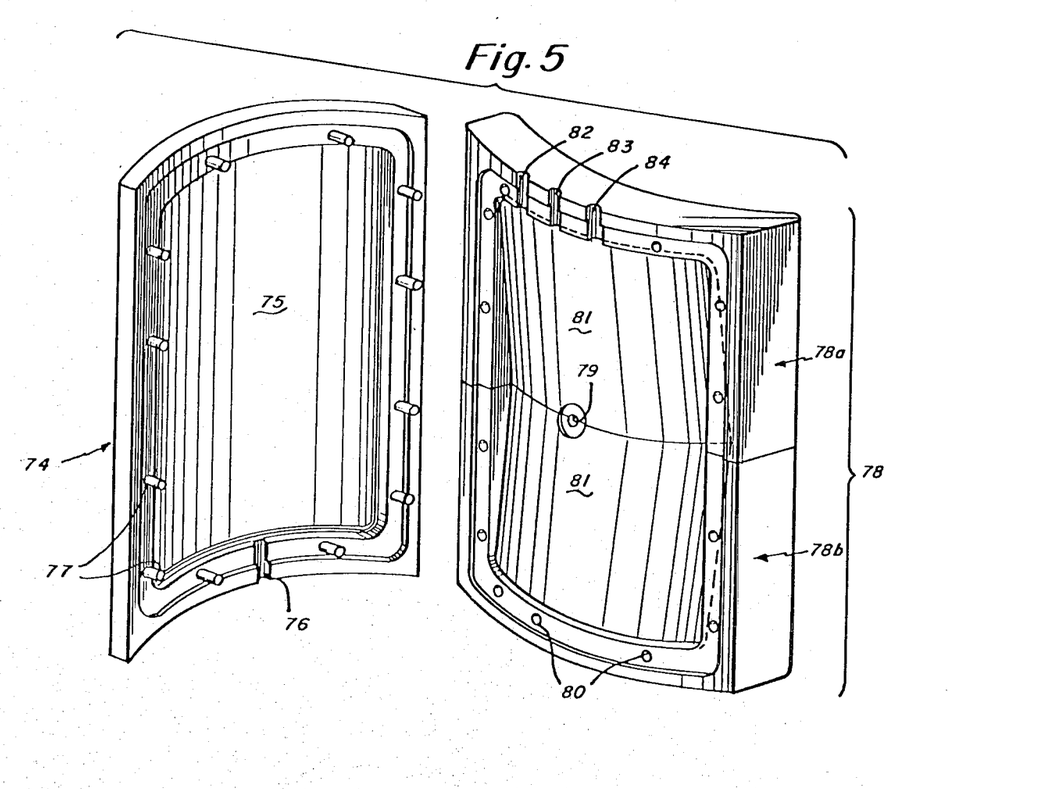
FIG. 5 is a perspective view of complementary support shoes for the blood processing bag and displacement pouch of FIGS. 3 and 4, respectively.

Blood processing bag 50 and flexible displacement pouch 69 are held in a complementary relationship in a contoured processing chamber formed between a pair of support shoes which are shown in FIG. 5.

Shoe 74 has an inner surface 75 having a generally cylindrical shape approximately concentric with the geometrical axis of rotation. Inner surface 75 contacts the radially outward face of pouch 69 during processing. Channel 76 is provided in shoe 74 to allow displacer fluid tubing 73 to pass through the support shoes when they are held in their closed position. A pattern of pegs 77 is provided around the edge of support shoe 74, and the function of pegs 77 is described below.

Support shoe 78 is actually split into upper shoe half 78a and lower shoe half 78b, to allow tubing 60 to be inserted through hole 79 of shoe 78. This is necessary because the entire blood pathway, as illustrated in FIG. 2, is integral and disposable. Peg holes 80 are provided around the inner edge of shoe 78 to accommodate pegs 77 located around the inner edge of support shoe 74.

Inner surface 81 of shoe 78 has a somewhat cylindrical contour, but is additionally contoured to have a gentle slope from both its top and bottom towards a horizontal center line passing through hole 79 and is also contoured to have a gentle slope from both sides towards a verticle center line passing through hole 79. Such contoured sloping provides a centrifugal slope from all points so that separated first blood component is always directed towards outlet 59 of blood processing pouch 50 during centrifugation.

Channels 82, 83 and 84 provide access to the contoured processing chamber formed between shoes 74 and 78 when they are positioned together. Channels 82, 83 and 84 can be used therefore to pass tubing 45, 45' and 49 into the contoured processing chamber formed between support shoes 74 and 78 or to accommodate connections to tubing 45, 45' and 49.

Support shoes 74 and 78 can be formed from polymers such as foamed polyurethane. In some cases, it will be preferred to have transparent support shoes, in which case they can be formed from transparent polymers, such as poly(methyl methacrylate). Many other materials could be used in forming these support shoes, of course.

Pouch 69 is mounted on shoe 74 by inserting pegs 77 through registration holes 71 in the peripheral seal 70 of pouch 69; subsequently, processing bag 50 is mounted on pegs 77 in the same manner employing registration holes 55 while insuring that its port 59 is positioned radially inwardly. Shoes 74 and 78 are then closed together so that pegs 77 extend into matching holes 80 in the edge of shoe 78. In their closed position, shoes 74 and 78 form an enclosed contoured processing chamber containing blood processing bag 50 and fluid displacer pouch 69, which are positioned so that their contacting planar panels assume a complementary relationship.

When blood processing bag 50 and flexible pouch 69 are positioned in this complementary relationship within the contoured processing chamber formed between support shoes 74 and 78, pouch 69 serves as a displacement chamber having a fluid-actuated diaphram. As displacer fluid is introduced into pouch 69, it expands to force blood or blood components out of processing bag 50. Similarly, as anti-coagulated whole blood passes into blood processing bag 50 under positive pressure, an equal volume of displacer fluid is forced from the flexible displacement pouch 69.

The basic shape of the contoured processing chamber is an arc of a cylindrical annulus approximately concentric with the axis of rotation. The radial thickness of this chamber is minimized, and is preferably less than 15% of the peripheral length of the arc. The contour of the wall of the chamber on the side nearest the axis of rotation is modified from a true arc about this axis to provide a slope for natural drainage within the centrifugal field of the less dense plasma-rich component toward outlet port 59 located in the center of the radially inner face of blood processing bag 50. This is achieved by the centrifugal slope provided by the contoured surface 81 of support shoe 78.

Figures 6, 7:
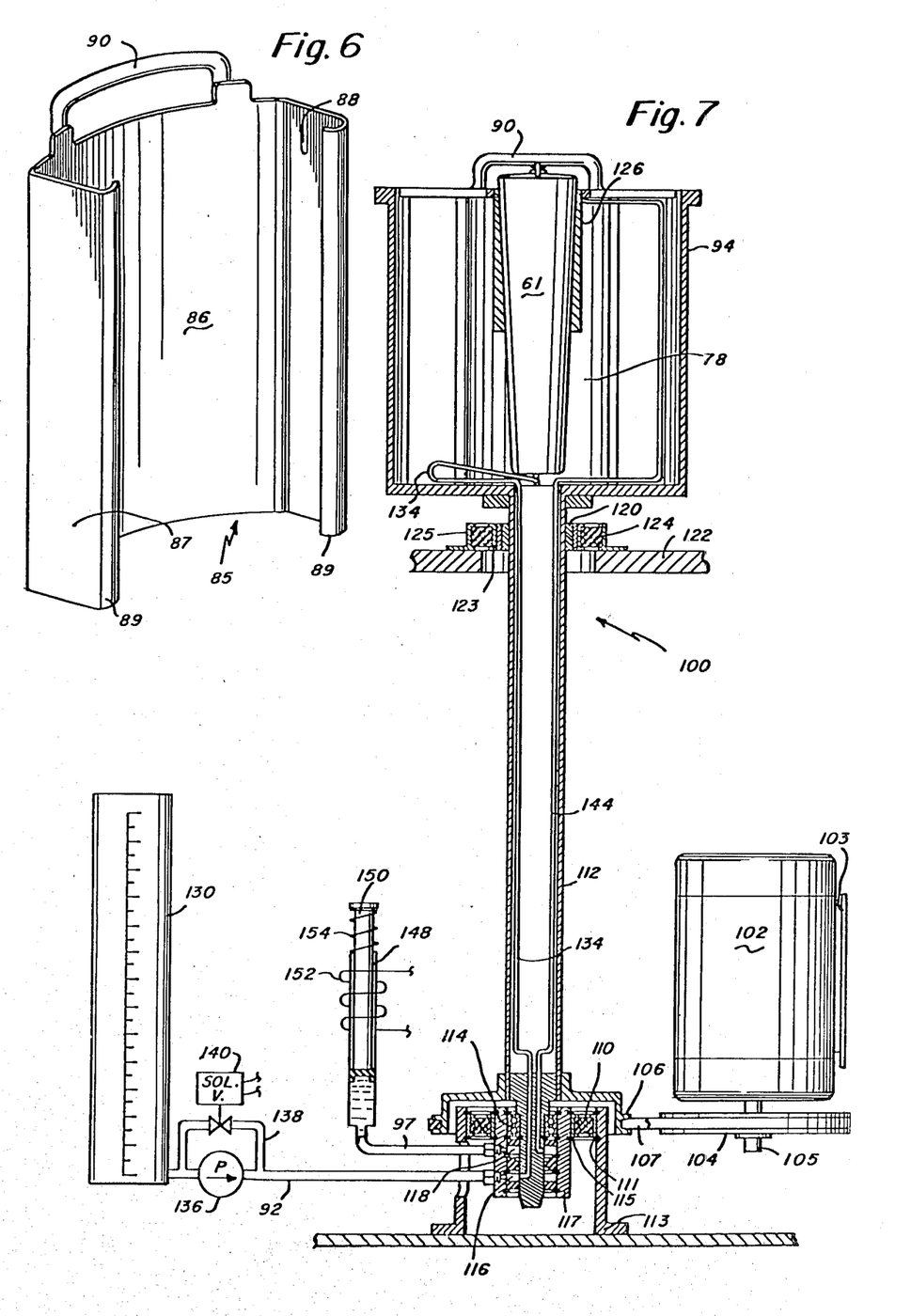
FIG. 6 is a perspective view of a holder for the support shoes of FIG. 5.
FIG. 7 is a partially cut-away front elevational view of a self-balancing centrifuge suitable for use in the apparatus of FIG. 1.

Support shoes 74 and 78 are held in a closed position by placing them in a support shoe holder 85 illustrated in FIG. 6. Holder 85 has a cylindrically shaped back wall 86, two side walls, 87 and 88, each of which has a curved lip 89 at its terminal portion which curls around to contain support shoes 74 and 78. Holder 85 is also provided with a handle 90 so that it can be conveniently lifted. Support shoe holder 85 can be formed from materials such as aluminum, etc.

A plasmapheresis procedure employing apparatus 10 is as follows. Prior to withdrawing blood from donor's arm 12, blood processing bag 50 is collapsed by filling pouch 69 completely with displacer fluid while tube 60 is tightly clamped. The displacer fluid distends bag 69, which in turn compresses processing bag 50 against inner surface 81 of shoe 78 to express any blood or blood components from bag 50.

Use of a fixed charge of displacer fluid passing in tubing 92 between a stationary displacer fluid station 93, external to centrifugal rotor 94, and displacer pouch 69 within rotor 94, allows the monitoring of the volume of blood introduced into blood processing bag 50 since the total volume of the displacer pouch and blood processing bag is constant. Thus, the amount of blood or components in blood processing bag 50 can be accurately determined by monitoring either changes in weight or volume of displacement fluid in displacer station 93.

When the desired amount of whole blood has been withdrawn from a donor, blood compatible tubing 49 is first sealed, such as can be done with a dielectric sealer, and then cut. This is typically done by sealing tubing 49 in two places and by cutting between the seals or by making a broad seal which is cut in the middle. Anti-coagulant pump 24 continues to slowly pump anti-coagulant through phlebotomy needle 16 at this point to prevent clot formation therein while blood is not flowing.

Centrifuge motor 102 is now activated to cause centrifuge rotor 94 to rotate at a speed sufficient to separate the withdrawn whole blood contained in processing bag 50 into a plasma-rich component and a plasma-poor component. A typical rotor speed, for example, might be about 4800 rpm.

As centrifuge rotor 94 rotates, plasma-poor component, which in this case consists primarily of red blood cells, white blood cells and platelets, moves towards the radially outer face of disposable blood processing bag 50. This creates plasma-rich component near the radially inner face, and this can be expressed from disposable processing bag 50 as centrifuge rotor 94 spins by introducing displacer fluid into displacement pouch 69 thereby applying pressure to disposable blood processing bag 50. Plasma-rich component is expressed through central port 59 of the flexible blood processing bag 50 and is transported in tubing 60 to receiver container 61 as rotor 94 continues spinning and further separation. Tubing 60 is preferably kept relatively short to prevent it from folding back upon itself when the software is positioned in the centrifuge rotor.

Whenever plasma-rich component is being expressed from blood processing bag 50, tube clamp 142 (FIG. 8) is released to permit flow through tubing 60 to receiver container 61. At all other times, clamp 142 is kept closed. Since the inlet for receiver container 61 is positioned at a point of maximum diameter, it is possible to withdraw material from receiver container 61 back into blood processing pouch 50 by withdrawing displacer fluid from displacement pouch 69 while clamp 142 is open. This operates as a safeguard in case material is expressed from blood processing pouch 50 beyond that where the cut is desired. An optical detector can be provided, if desired, to sense when the separation has been completed. Clamp 142 is hydraulically operated by fluid contained in hydraulic fluid reservoir 95 and supplied in line 97.

When the cut has been completed, centrifuge rotor 94 is braked to a stop. A protective cover, if present, is removed from bag spike 46' and also from spike port 56 in blood processing bag 50. Slide clamp 47' on bag spike 46' is opened just long enough to allow spike 46' to prime with blood from blood tubing 45'. At this point, spike 46' is inserted into spike port 56 at the top of flexible, disposable blood processing bag 50 and slide clamp 47' is fully opened.

Plasma-poor component can now be returned to the donor by opening blood pump platen 38, and introducing displacer fluid into displacement pouch 69. Displacer fluid is transported to pouch 69 until it is once again filled with displacer fluid indicating that all of the plasma-poor component has been returned to the donor. This can be determined by measuring the amount of displacer fluid transported from stationary displacement station 93.

In the return cycle, monitor pouch 30 fills with plasma-poor component. Pressure detector 34 senses any undesirable build-ups of pressure in the system, which might be caused, for example, by a restriction at the tip of phlebotomy needle 16. When such a build-up is sensed, an appropriate signal can be transmitted to slow or halt the transport of displacer fluid to pouch 69. Optionally, an audible or visual alarm may be given.

When the plasma-poor component has been returned to the donor, a second whole blood withdrawal can be initiated. This can be done similarly to the first withdrawal cycle, except that the whole blood now flows through spike port 46' and into the top of disposable, flexible blood processing pouch 50 through port 56. After the desired amount of anti-coagulated whole blood has been introduced into disposable, flexible blood processing bag 50, blood compatible tubing 45' is sealed and cut, as before. Processing can now commence in a manner similar to that previously described.

At the end of the separation, centrifuge rotor 94 is stopped, the protective covers from bag spike 46 and spike port 58 are removed, slide clamp 47 is opened just long enough to allow spike 46 to prime with blood, and then spike 46 is inserted into spike port 58. Slide clamp 47 is fully opened and plasma-poor component remaining in flexible, disposable blood processing pouch 50 is returned to the donor, as before.

In a typical plasmapheresis separation as described, 500 ml of whole blood can be withdrawn in each withdrawal cycle. Each centrifuge cycle can produce about 250 ml of plasma-rich component having a small amount of anti-coagulant therein. This plasma-rich component is essentially free of other components. The plasma-poor component can be returned to the donor and would typically consist of something like about 84% red blood cells, 1% platelets and about 15% plasma—it would also contain a small amount of anti-coagulant. Thus, after two withdraw cycles of 500 ml of whole blood each, and two separation and return cycles, approximately 500 ml of plasma remain in the plasma receiver. The time for carrying out the entire procedure is likely to be thirty minutes or less.

Unbalance in centrifuge rotor 94 is minimized, even though fluid is being introduced and withdrawn during its operation, since the total volume of fluid, within the assymetric portion of the fluid pathway, namely blood plus displacer fluid, remains constant. To further minimize unbalance, it is preferable to employ displacer fluid having a density close to that of whole blood, such as within ±15% of the density of whole blood. It is further preferred, if displacer pouch 69 is located radially outwardly, to employ displacer fluid having a density greater than that of the second blood component—this helps to maintain a generally cylindrical interface between the displacer pouch 69 and blood-processing bag 50 and minimizes any tendency for the processing bag 50 to be pinched off during return of second blood component to a donor. As an example, in a plasmapheresis separation, a displacer fluid density of about 1.1 would be suitable since typical specific densities for whole blood, packed cells and plasma are approximately 1.06, 1.09 and 1.05, respectively. On the other hand, it might be desirable in some cases to locate the displacement pouch on the radially inner side of a blood processing bag, in which case it would be preferred to employ displacer fluid with a density lower than the lightest blood component formed during separation.

The shape of receiver container 61 and its positioning within rotor 94 also minimize imbalance in the centrifuge. As can be seen, fluid present in receiver container 61 while rotor 94 is spinning is evenly distributed about the axis of rotation. Other receiving containers for a separated blood component can be used, of course, but it is preferable to employ one or more receiver containers which attain a substantially even distribution of fluid therein about the axis of rotation.

It is preferable to employ blood-compatible materials for all tubing, pouches, bags, etc., in this apparatus if they come into contact with blood or a component thereof. An example of such a material is polyethylene. In some cases, such as those where tubing is cut and sealed, it is particularly preferred to employ a blood-compatible, heat-sealable material, such as poly(vinyl chloride). It is also preferable, in many cases, to form pouches and bags from transparent materials to permit visibility during processing.

Figure 8:
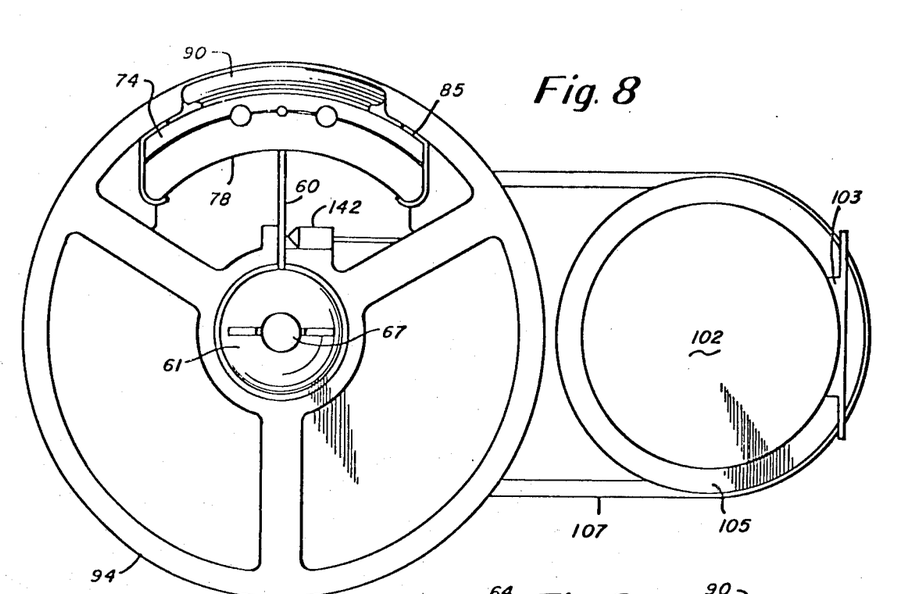
FIG. 8 is a plan view of the centrifuge of FIG. 7.
Figure 9:
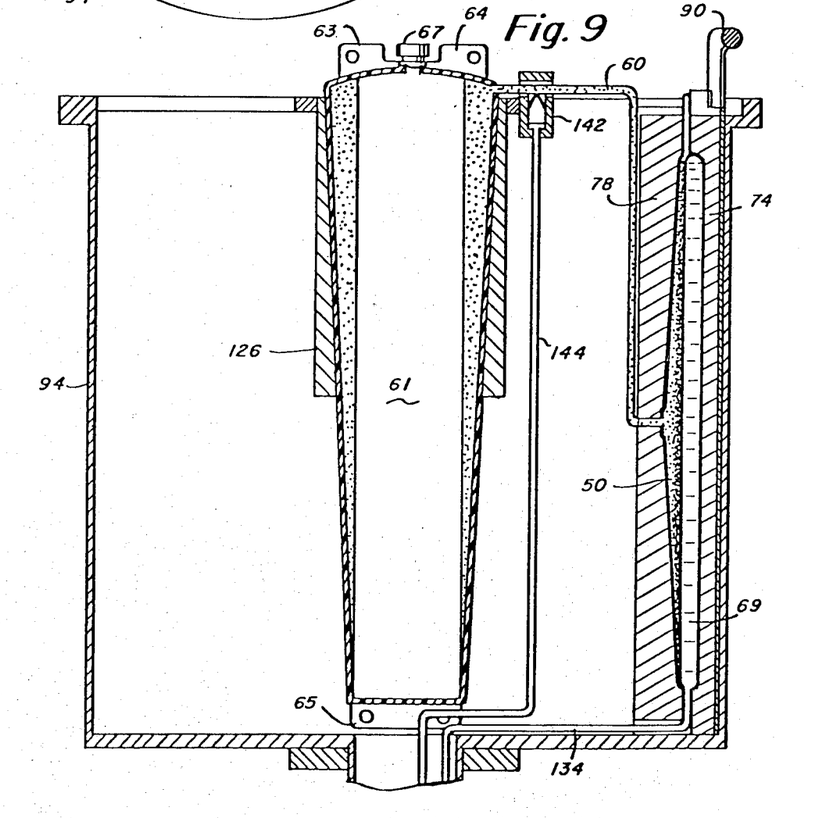
FIG. 9 is a partially cut-away side elevational view of the centrifuge rotor with a portion of the disposable blood pathway shown in FIG. 2 contained therein; and, FIG. 10 is a partially cut-away side elevational view of a centrifuge rotor containing a blood processing bag having an alternative geometry together with a complementary displacement bag and a receiver container.

One self-balancing centrifuge suitable for use in the invention described herein is illustrated in more detail in FIGS. 7-9. Therein, centrifuge 100 can be driven by a standard electric motor 102, which may be fixed or variable speed. Preferably, motor 102 is vibration isolated and mounted to a rigid structure through mounting plate 103. Drive pully 104, attached to motor drive shaft 105, drives centrifuge drive pully 106 via drive belt 107.

A pivot mount is positioned in the plane of pulleys 104, 106 and belt 107 to eliminate significant turning moments in planes coincident with the axis of rotation. A suitable pivot mount can be formed from an elastomeric ring 110 of soft silicone rubber or other similar material mounted within an outer metallic ring member 111 attached to stationary mount 113 and an inner metallic ring member 115 attached to stationary housing 117. This pivot mount allows centrifuge 100 to find its own center of rotation around its angular momentum vector, while still providing some resistance to undesired movement of centrifuge shaft 112.

The bottom end of centrifuge shaft 112 is journaled in radial ball bearings 114. Shaft 112 is a thin walled tube with good stiffness but one which is light in weight, such as can be formed from stainless steel tubing. Rotary seals 116 and 118 provide communication between stationary metallic fluid lines 92 and 97 and internal flexible tubing 134 and 144, respectively, the functions of which are described below.

An oiled porous bearing 120 acts as a damped, resilient retraining mount employed near the top of shaft 112 to provide a slight righting force. Bearing 120 is formed by inner ring member 123 and outer ring member 125 with spongy elastomer material 124 therebetween. Outer ring member 125 is rigidly secured to support 122. Elastomeric material 124 acts as a light spring and damper, and allows the spring constant and dampening to be independently controlled. Open cell elastomeric foam is preferred.

Receiver container 61 is located within centrifuge rotor 94 in tapered conical holder 126. Rotor 94 can be formed from aluminum and may be provided with a protective polymethyl methacrylate guard. Access to rotor 94 is conveniently provided through its top.

An optical slit (not shown) positioned directly beneath tubing 60 and a strong projection lamp secured in a stationary location under rotor 94 may be used to provide synchronized illumination of tubing 60. Alternately, a sychronized stroboscopic light may be used to illuminate the entire interior of rotor 94.

Displacer fluid at station 93 can be stored in a transparent graduated reservoir 130 which facilitates measurements of the amount present. It is transported to displacer pouch 69 in metal tubing 92 and flexible tubing 134 which are coupled at rotary seal 116. Flexible tubing 134 runs up through shaft 112 to displacement pouch 69. Displacer fluid pump 136 is used to transport displacer fluid from reservoir 130 to displacer pouch 69. The return of displacer fluid is achieved by inactivating pump 136 and opening solenoid valve 140 in by-pass line 138 whereby blood filling bag 50 operates to force displacer fluid from pouch 69 and back to reservoir 130 through lines 134, 92 and 138.

Hydraulically actuated clamp 142 is connected by flexible tubing 144 and rigid tubing 94, coupled through rotary seal 118, to hydraulic fluid cylinder 148. Hydraulic pressure is applied by piston 150 which can be operated in the forward direction by solenoid 152 and in the return direction by spring 154.

FIG. 9 illustrates blood components as they might occur in an on-going plasmapheresis cycle. Processing bag 50 contains plasma-poor component, which would typically be packed red cells, indicated by dark stippling, toward its outer radial portion. Plasma-rich component is located radially inwardly and is indicated by light stippling. The plasma-rich component is also shown in tubing 60 and receiver container 61 as it would appear towards the end of a plasmapheresis cycle.

Plasma-rich component is expressed from processing bag 50 into receiver container 61 by the action of displacement bag 69 which is partly filled with displacer fluid and has a surface contacting bag 50 so that this surface acts as a fluid-operated diaphram. Receiver container 61 is provided with a sterile air filter 67 on its top cover to allow any air present in the system to escape.

Figure 10:
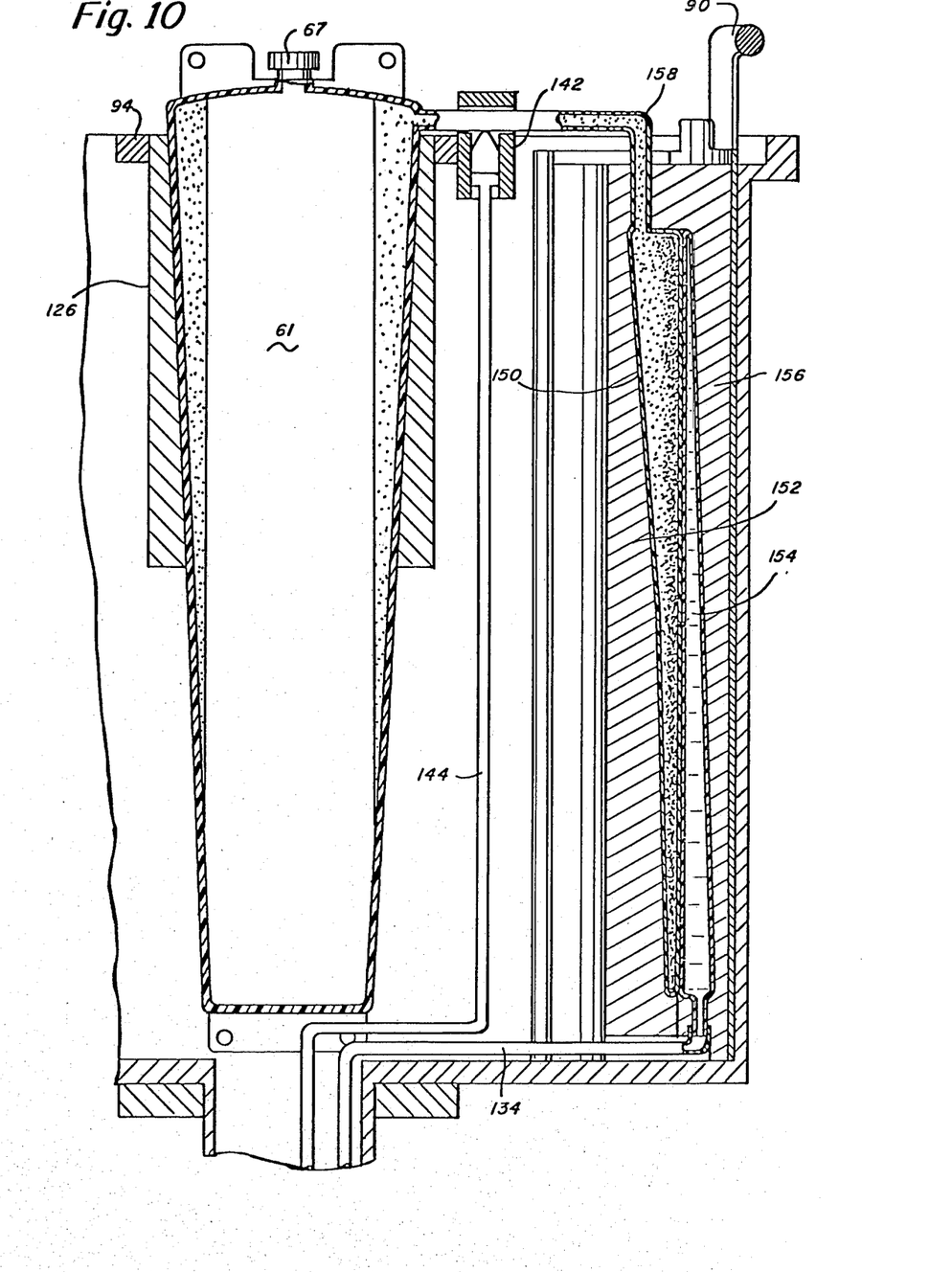

FIG. 10 illustrates an alternative embodiment in which flexible, disposable blood processing bag 150 is supported by contoured shoe 152 so that bag 150 has an inner surface having a slightly greater slope at its upper portion than at its lower portion. This increased slope provides more efficient emptying during operation. Displacer pouch 154 is contoured into a complementary shape by support shoe 156. Other elements are the same as previously described. This embodiment permits use of tubing 158, connecting bag 150 to receiver container 61, at the top of bag 150. Thus, support shoe 152 does not have to be split. Displacer pouch 154 can be permanently mounted, if desired, in this or previously described embodiments.

Those skilled in the art will recognize many equivalents to the specific embodiments described herein. Such equivalents are considered part of this invention and are intended to be covered by the following claims.

What is claimed is:

1. A disposable blood pathway for use in the centrifugal separation of blood in a spinning centrifuge rotor into a first blood component and a second blood component comprising, in combination:
    a flexible blood processing bag having at least one inlet port and one outlet port, said flexible blood processing bag having inner and outer wall members with a relatively small distance between said inner and said outer wall members compared to other internal bag dimensions so that the distance blood components travel during centrifugal separation is minimized when said bag is supported in the centrifuge rotor in a position whereby said relatively small distance is positioned transverse to the axis of rotation so that second blood component travels along this short internal bag dimension during centrifugal separation;
    a receiver container for receiving first blood component separated in said flexible blood processing bag, said receiver container having at least one inlet port and having a geometry which minimizes imbalance in said centrifuge rotor as separated first blood component is introduced into the receiver container;
    blood-compatible tubing connecting an outlet port of said flexible blood processing bag with an inlet port of said receiver container; and
    blood compatible tubing for providing fluid communication between a source of blood to be separated and an inlet port on said flexible blood processing bag.

2. A disposable blood pathway of claim 1 wherein said blood processing bag has an outlet for separated first component located at approximately the center of its inner wall member.

3. A disposable blood pathway of claim 2 wherein said blood processing bag has an inlet for blood to be separated at the top thereof and at least one port for removal of said second blood component therefrom after separation.

4. A disposable blood pathway of claim 3 wherein said blood processing bag has two sealed spike ports for reconnection and said blood compatible tubing providing fluid communication between said source of blood and the inlet port of said disposable blood processing bag is dielectrically sealable and additionally contains two sealed insert spikes adapted for insertion into the two sealed spike ports of said disposable blood processing bag.

5. A disposable blood pathway of claims 1 or 4 wherein said receiver container has the form of a volume of revolution with the upper end larger than its lower end and a inlet port for first blood component at a point of substantially maximum diameter of said container.

* * * * *

UNITED STATES PATENT AND TRADEMARK OFFICE
CERTIFICATE OF CORRECTION

PATENT NO. : 4,285,464
DATED : August 25, 1981
INVENTOR(S) : Allen Latham, Jr.

It is certified that error appears in the above—identified patent and that said Letters Patent is hereby corrected as shown below: On the title page item 62 should read:

---[62] Division of Ser. No. 5,126, Jan. 22, 1979 issued on December 1, 1981 as U. S. Patent No. 4,303,193.---

Signed and Sealed this

Twelfth Day of October 1982

[SEAL]

Attest:

GERALD J. MOSSINGHOFF

Attesting Officer     Commissioner of Patents and Trademarks